US012642691B2

(12) United States Patent
Leblanc et al.

(10) Patent No.: US 12,642,691 B2
(45) Date of Patent: Jun. 2, 2026

(54) DEVICES AND METHODS FOR SLEEP APNEA AND SNORING

(71) Applicant: LeBlanc Dental Products, Inc., Spring, TX (US)

(72) Inventors: Kelly Leblanc, Magnolia, TX (US); Charles Houssiere, Houston, TX (US); Jessica Buell, Rowley, MA (US); Kimberly Najjar, Houston, TX (US)

(73) Assignee: LeBlanc Dental Products, Inc., Houston, TX (US)

( * ) Notice: Subject to any disclaimer, the term of this patent is extended or adjusted under 35 U.S.C. 154(b) by 376 days.

(21) Appl. No.: 17/795,742

(22) PCT Filed: Jan. 28, 2021

(86) PCT No.: PCT/US2021/015402
§ 371 (c)(1),
(2) Date: Jul. 27, 2022

(87) PCT Pub. No.: WO2021/154930
PCT Pub. Date: Aug. 5, 2021

(65) Prior Publication Data
US 2023/0086923 A1 Mar. 23, 2023

Related U.S. Application Data

(60) Provisional application No. 62/966,797, filed on Jan. 28, 2020.

(51) Int. Cl.
*A61F 5/56* (2006.01)
(52) U.S. Cl.
CPC .................................... *A61F 5/566* (2013.01)

(58) Field of Classification Search
CPC ...... A61F 2005/563; A61F 5/566; A61F 5/00; A61F 5/56; A61C 5/00; A61C 5/007; A61C 7/00; A61C 7/08; A61C 7/36; Y10S 602/902
USPC ........ 128/848, 859, 861, 862; 433/6, 18, 19; 602/902
See application file for complete search history.

(56) References Cited

U.S. PATENT DOCUMENTS

| | | | | | |
|---|---|---|---|---|---|
| 5,570,704 | A | * | 11/1996 | Buzzard | A61F 5/566 |
| | | | | | 128/848 |
| 5,823,194 | A | * | 10/1998 | Lampert | A61F 5/566 |
| | | | | | 128/859 |
| 5,941,247 | A | * | 8/1999 | Keane | A61F 5/566 |
| | | | | | 128/859 |

(Continued)

FOREIGN PATENT DOCUMENTS

| | | | | | |
|---|---|---|---|---|---|
| FR | 2962897 | A1 | * | 1/2012 | A61C 7/08 |

OTHER PUBLICATIONS

FR 2962897 A1 machine translation (Year: 2012).*

*Primary Examiner* — Caitlin A Carreiro
(74) *Attorney, Agent, or Firm* — Equip LG; Christopher Quan

(57) ABSTRACT
A Mandibular Advancement Device (MAD) is disclosed which is useful for the treatment of snoring and Obstructive Sleep Apnea (OSA). The improved MAD design comprises upper and lower splints which can be set at an advanced protrusive position (as desired for snoring/OSA therapy), but which also permits some degree of lateral mandibular movement. The amount of protrusive mandibular advancement is adjustable.

20 Claims, 6 Drawing Sheets

(56)         References Cited

U.S. PATENT DOCUMENTS

| | | | |
|---|---|---|---|
| 6,983,752 B2 | 1/2006 | Garabadian | |
| 10,251,729 B1 | 4/2019 | Raslambekov | |
| 10,583,032 B2 | 3/2020 | Rogers | |
| 2005/0199247 A1* | 9/2005 | Garabadian | A61F 5/566 |
| | | | 128/848 |
| 2009/0308401 A1 | 12/2009 | Rosenblum | |
| 2010/0261133 A1 | 10/2010 | Lax | |
| 2012/0145166 A1 | 6/2012 | Fallon | |
| 2013/0098372 A1 | 4/2013 | Webster et al. | |
| 2014/0120489 A1 | 5/2014 | Klein | |
| 2014/0130809 A1* | 5/2014 | Lindsay | A61F 5/566 |
| | | | 128/848 |
| 2015/0182374 A1 | 7/2015 | Stenberg et al. | |
| 2017/0035533 A1 | 2/2017 | Ross | |
| 2018/0360646 A1 | 12/2018 | Bedford | |
| 2019/0021901 A1* | 1/2019 | LeBlanc | A61C 7/36 |

* cited by examiner

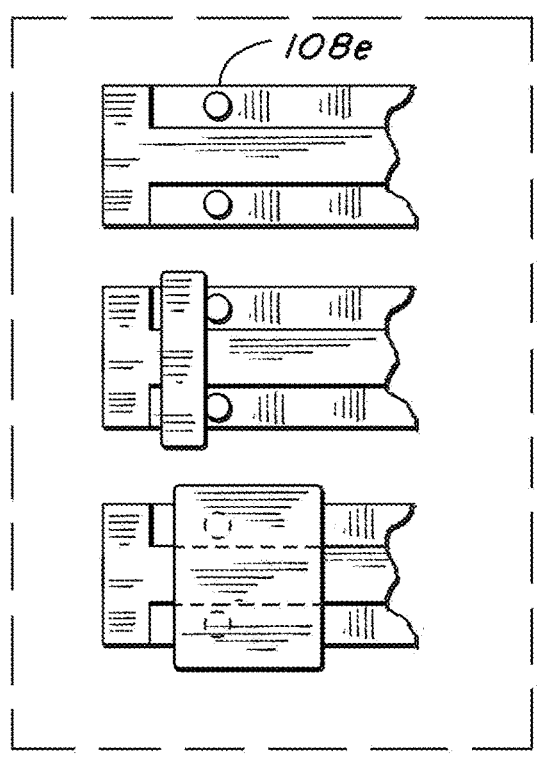
Fig.4a
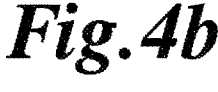
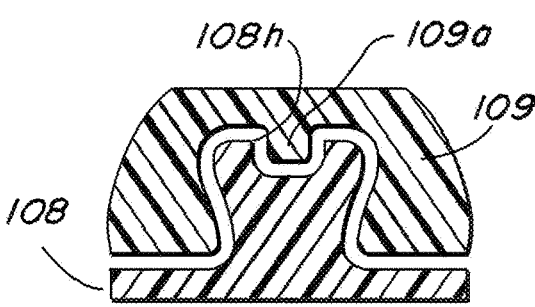
Fig.4b
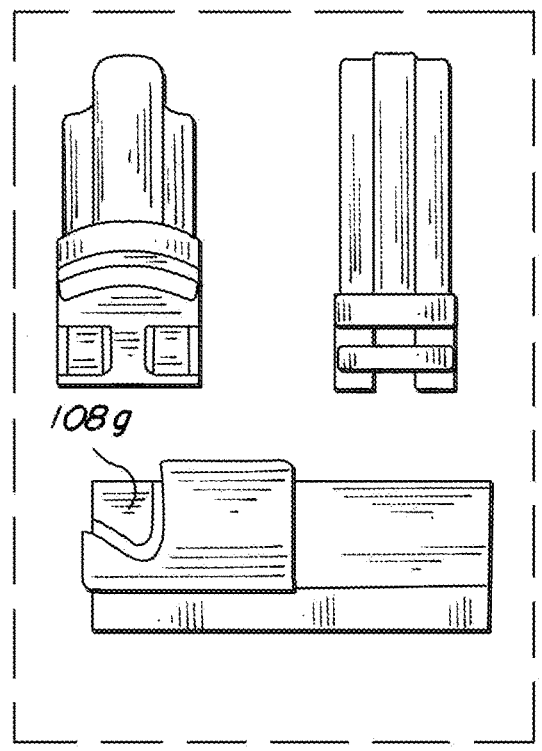
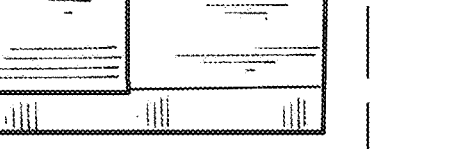
Fig.4c
Fig.4d

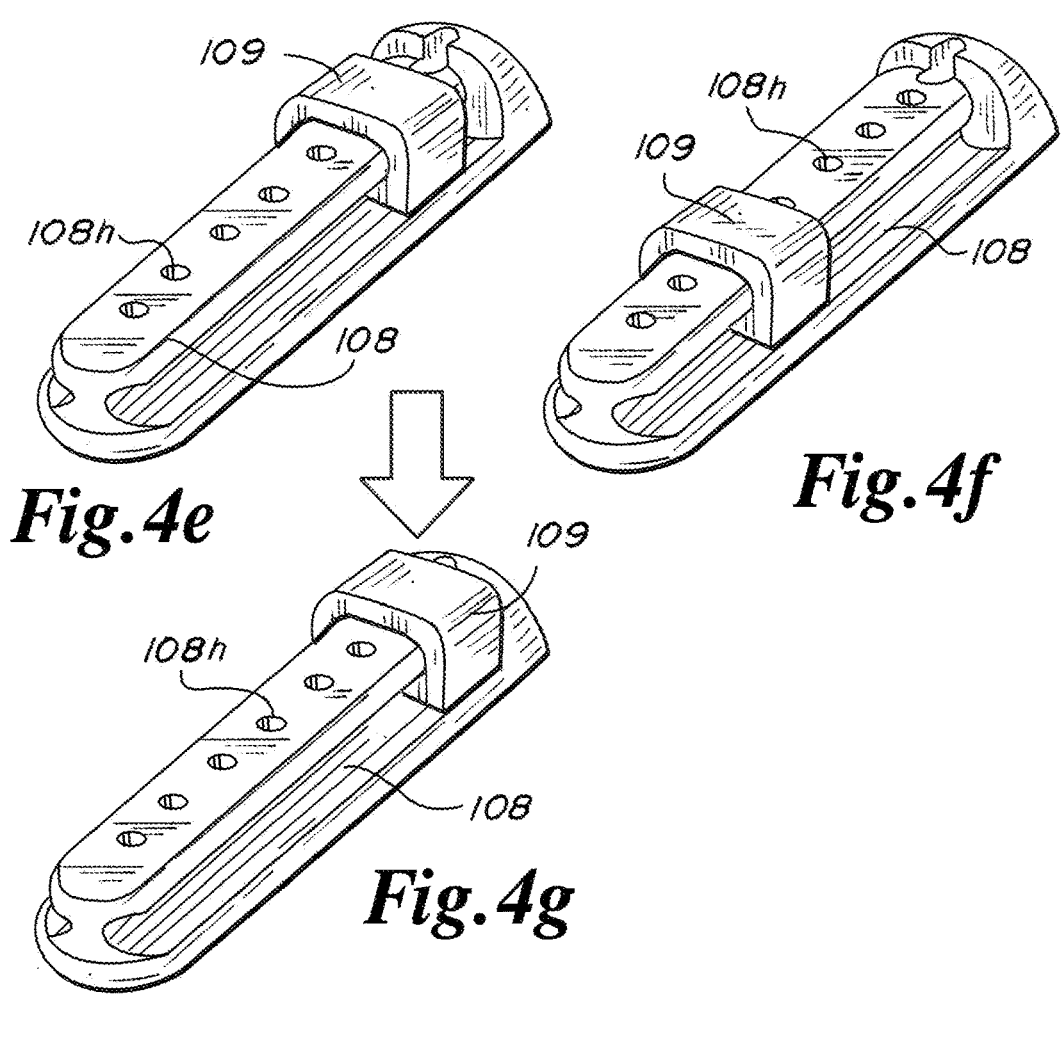
*Fig.4e*
*Fig.4f*
*Fig.4g*
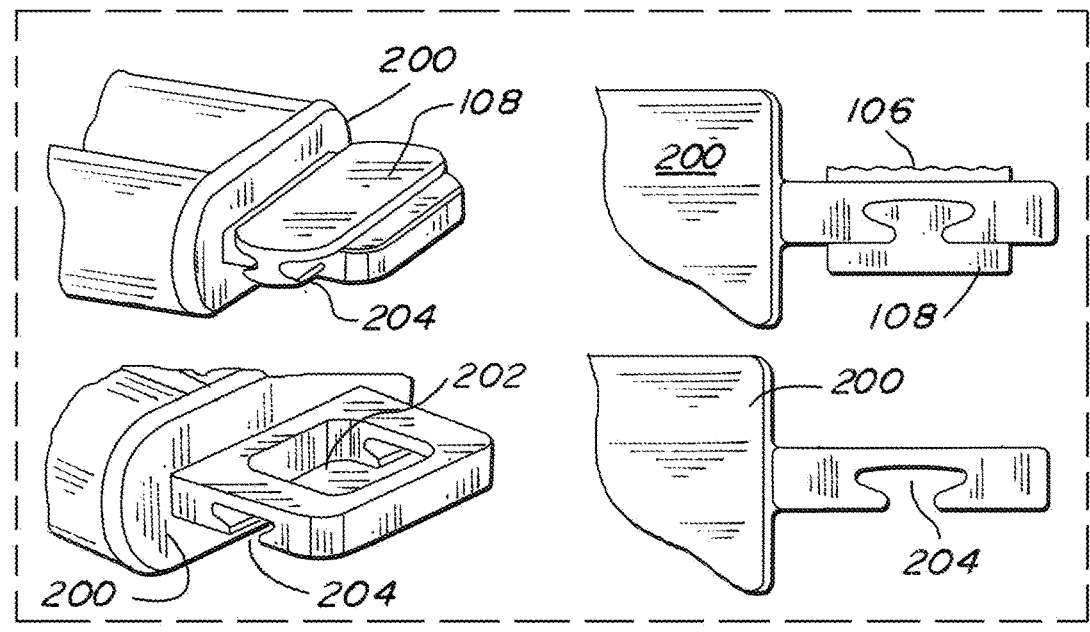
*Fig.5*

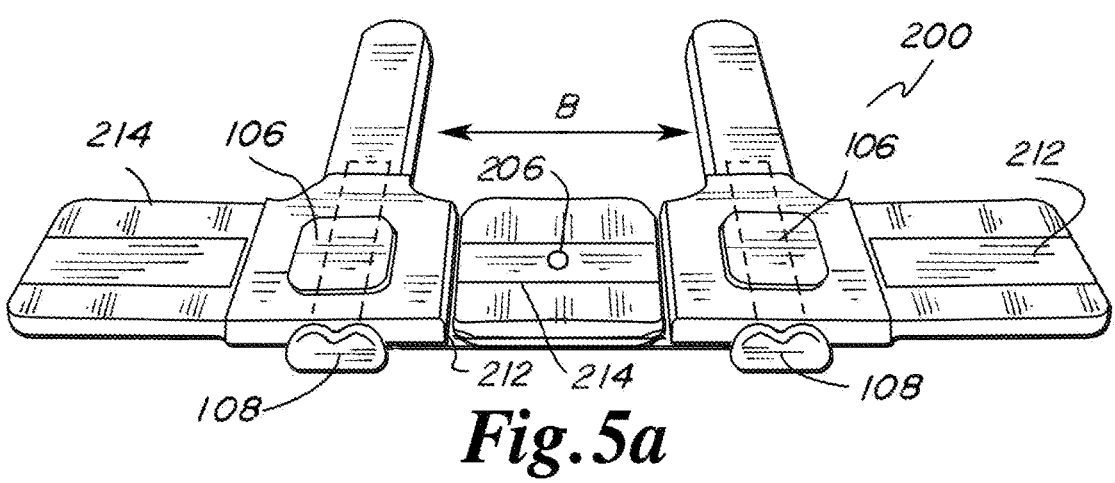
*Fig.5a*
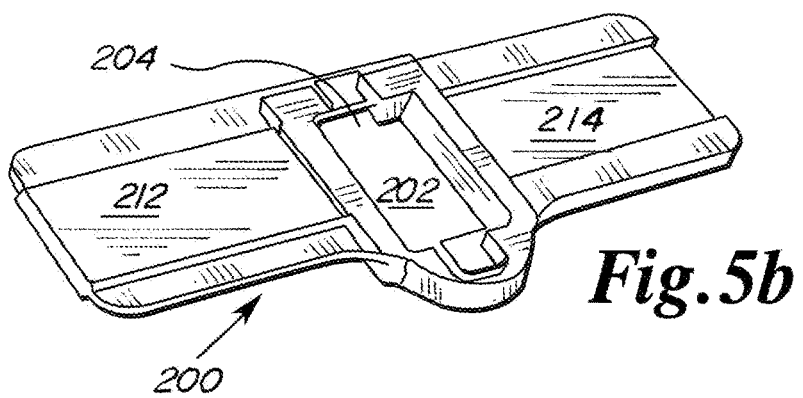
*Fig.5b*
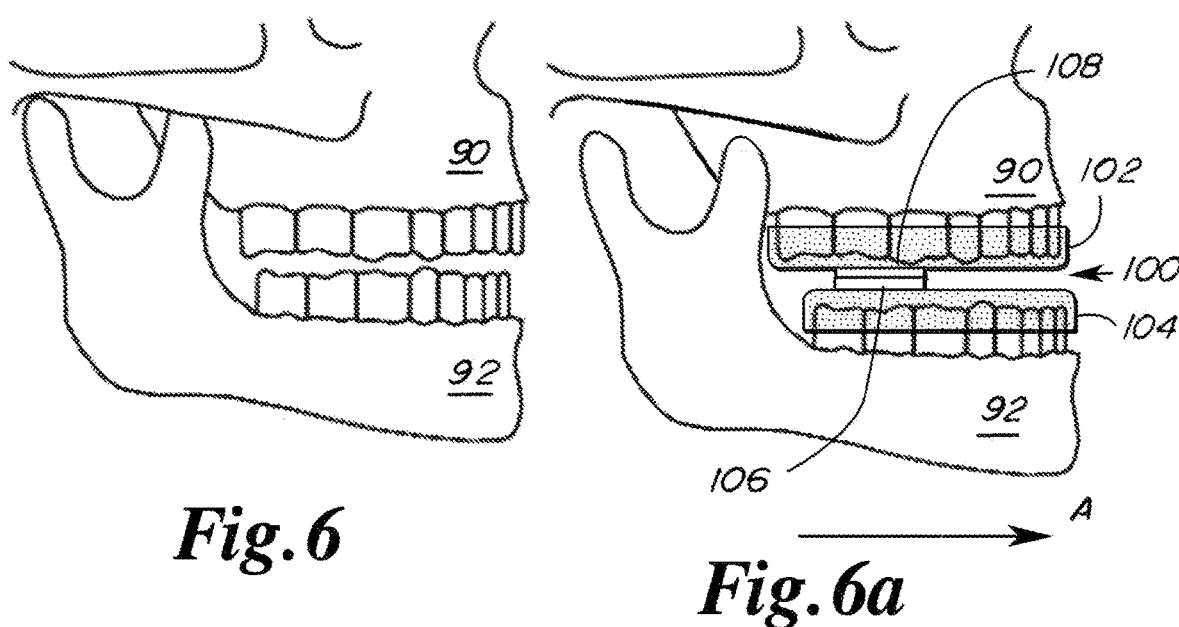
*Fig.6*
*Fig.6a*

DEVICES AND METHODS FOR SLEEP APNEA AND SNORING

CROSS-REFERENCE TO RELATED APPLICATIONS

This application is a 371 national stage application of Patent Cooperation Treaty international application Ser. No. PCT/US21/15402, which claims the benefit and priority of U.S. provisional patent application Ser. No. 62/966,797, filed Jan. 28, 2020, entitled, "DEVICES AND METHODS FOR SLEEP APNEA AND SNORING", the contents of all of which are hereby incorporated by reference in their entireties.

FIELD OF THE INVENTION

This invention relates to devices and methods for treatment of sleep apnea and snoring, particularly to devices and methods for mandibular adjustment, and more particularly to devices and methods for adjustable and/or customizable mechanisms for positioning and retaining the upper and lower splints of a mandibular adjustment device.

BACKGROUND OF THE INVENTION

Snoring is a sound produced by the vibration of soft tissue in a patient's upper airway caused by breathing obstruction during sleep. There are many factors associated with snoring including, but not limited to: heredity, body weight, age, gender, smoking history, tissue deformities, alcohol use, allergies, and sleep position. Commonly, the snorer, and perhaps the snorer's sleep partner, lose sleep due to the snorer's snoring. Lack of sleep can lead to daytime fatigue, a compromised immune system, poor mental and emotional health, irritability and lack of productivity, as well as other problems.

Obstructive Sleep Apnea ("OSA") is a potentially lethal sleep and breathing disorder defined as the cessation of breathing for a certain length of time (10 seconds or longer) and with a certain frequency. When breathing is interrupted, the body reacts by waking enough to start breathing again. Episodes may occur hundreds of time each night, and may not fully awaken the individual, who remains otherwise unaware of the loud snoring, choking and gasping for air typically associated with OSA. The health risks of OSA include higher risks or occurrences of hypertension, heart attack, stroke, daytime somnolence, depression, fibromyalgia, cardiac arrhythmia, inefficient metabolism, loss of short term memory, weight gain, gastric reflux, high blood pressure, diabetes, severe anxiety, memory and concentration impairment, morning headache, intellectual deterioration, mood swings/temperamental behavior, insomnia, and impotence. Additionally, many OSA sufferers do not receive a sufficient amount of sleep due to repeated apnea events and arousals which act to prevent deep stage sleep, which can lead to chronic daytime exhaustion. An estimated 40 million Americans suffer from some degree of OSA, yet only a small fraction of these are currently undergoing any type of treatment.

Snoring and OSA are generally caused by blockage of the upper airway when various tissues relax, including the tongue, uvula, and soft palate. Snoring is caused by the partial obstruction of breathing during sleep, while OSA occurs when the tongue and soft palate collapse onto the back of the throat and completely block the upper airway, thereby stopping breathing and restricting the flow of oxygen.

Many techniques exist to reduce or eliminate snoring and OSA. Various types of surgery, including tracheostomy, surgery of the soft palate and oropharynx, and reconstructive surgery have been utilized in the treatment of snoring and OSA. Surgery however is costly, carries risks, and is not always effective.

Respiratory therapies for the treatment of OSA have been utilized as well, generally utilizing a ventilator type mask on the patient that supplies air/oxygen at a higher than atmospheric pressures, generally known as Continuous Positive Air Pressure systems or CPAP systems. Variations of this therapy having variable pressures have also been used, such as Bi-level Positive Air Pressure (BiPAP) or Multiple Positive Air Pressure (MPAP) systems. These systems however suffer from significant patient non-compliance, because patients often find it difficult to acclimatize to the mask and the pressures they provide. These systems can also be noisy, and can also affect the patient's sleeping partner, even to the point that the patient and the sleeping partner will sleep in separate rooms to each have an effective night of sleep. In other words, patients often dislike and therefore stop using respiratory therapies of these types.

Another class of snoring/OSA solutions includes appliances that patients wear to reposition theirs jaws to inhibit their airways from closing. Such devices are generally referred to as Mandibular Advancement Devices (MADs) or Mandibular advancement splints. A MAD treats snoring and OSA by advancing the mandible (lower jaw) forward slightly in a protrusive (generally horizontal) direction relative to the maxilla (upper jaw). This tightens the soft tissue of the upper airway to prevent obstruction during sleep. Such tightening also inhibits these tissues from vibrating as air passes over them, thus reducing snoring. MADs are generally less cumbersome than respiratory therapy systems (CPAP, BiPAP, etc.), which promotes high patient compliance. MADs may be prescribed by different types of physicians, but given that they are worn on the teeth, MADs are generally produced and fit under the direction of dentists, orthodontists and the like.

SUMMARY OF THE INVENTION

This invention relates to devices and methods for treatment of sleep apnea and snoring, particularly to devices and methods for mandibular adjustment, and more particularly to devices and methods for adjustable and/or customizable mechanisms for positioning and retaining the upper and lower splints of a mandibular adjustment device (MAD).

In general, a MAD device may include an upper splint and a lower splint, each for retaining at least a portion of a person's upper jaw (maxilla) and lower jaw (mandible), respectively. The splints may generally be formed to fit and contour to the jaws of a particular person, such as through the use of dental impressions, however, standardized or generic splints may also be utilized. The upper and lower splints may generally be operatively coupled together in an arrangement that promotes the positioning of the lower splint, and thus the lower jaw of the person, in a more forward position relative to that of the upper splint and jaw in a generally horizontal direction.

In one aspect of the invention, the MAD may include an adjustable mechanism that may vary the relative positioning of the upper and lower splints. The adjustable mechanism may generally set the relative horizontal differential between the upper and lower splints such that the lower splint may be set to a desired forward horizontal position relative to the upper splint to treat apnea and/or snoring through protrusive positioning of the lower jaw. In some exemplary embodiments, the adjustable mechanism may include a rail portion attached to one splint and a corresponding groove portion attached to the other splint, with the rail portion and the groove portion mating or interfacing such that the rail portion may slide along the groove portion (or vice versa) to alter the relative positioning of the upper and lower splints. The groove and rail portions may also be shaped in a manner such that the rail portion is retained in the groove portion to prevent the upper and lower splints from separating during use, such as, for example, using corresponding shapes (e.g. male-female connections).

In some embodiments, at least two sets of rail and groove portions may be included to connect the upper and lower splints. For example, one set may be present on each of the left and right sides of the jaws. The rail and groove portions may generally be attached to upper and lower splints at positions that enable the proper alignment and interfacing of the rail and groove portions.

In other embodiments, there may be only one set of rail and groove portions connecting the upper and lower splints.

The rail or groove portion may also generally include a stop to prevent the relative positioning of the upper and lower splints from progressing past a given point. In some embodiments, the rail portion may include a stop, such as a portion that does not fit into the groove portion. The stop position may further be adjusted, for example, by placing spacers on the rail portion that may generally extend the stop portion that does not fit into the groove portion. Spacers may, for example, be of predetermined or metered size, and may be inserted as necessary to vary the stopped position of the lower splint relative to the upper splint. The spacers and/or the rail portion may also include features to aid in locking the spacers in place such that they are retained on the rail portion.

In another aspect of the invention, the MAD may include features for enabling small amounts of movement between the upper and lower splints. It may be desirable for the connection between the upper and lower splints to be not completely rigid such that the person wearing the MAD may have some degree of jaw mobility, such as to accommodate patients who grind their teeth (bruxism), which involves lateral left/right movement of the lower teeth (mandible) relative to the upper teeth (maxilla), or to aid in, for example and without being bound to any particular theory, preventing stress the Temporomandibular Joint (TMJ), which may cause long term soreness. In some exemplary embodiments, the corresponding shapes of the rail and groove portions of the adjustable mechanism may include some space between them, such as, for example, by the shape of the rail portion being smaller than the corresponding shape of the groove portion, such that one portion may move laterally and/or vertically to some degree while interfaced.

In a further aspect of the invention, the adjustable mechanism may be mounted to the MAD utilizing a device that enables adjustment of the positioning and/or orientation of the adjustable mechanism relative to the upper and lower splints such that the proper horizontal movement is enabled. In some exemplary embodiments, a mounting device may include an aperture for the groove portion of the MAD to pass through to retain the groove portion and an aperture for insertion of the rail portion such that the rail portion may also interface with the groove portion. This may be utilized during the attachment of the adjustable mechanism to the upper and/or lower splint(s) to ensure their proper alignment and positioning when they are attached, such as, for example, to accommodate non-parallel interfacing of the upper and lower splints. The mounting device may also include an adjustable section such that the mounting device may be adjusted in size laterally to accommodate different widths of the splints, which may vary due to differing jaw shapes and sizes from different people. In some exemplary embodiments, the mounting device may be constructed from two identical components, each of which may include a male and female portion to enable interfacing with another identical component in a different orientation. This may be utilized, for example, to form the adjustable section.

The present invention together with the above and other advantages may best be understood from the following detailed description of the embodiments of the invention and as illustrated in the drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE FIGURES

The drawings accompanying and forming part of this specification are included to depict certain aspects of the invention. A clearer impression of the invention, and of the components and operation of systems provided with the invention, will become more readily apparent by referring to the exemplary, and therefore non-limiting, embodiments illustrated in the drawings, wherein identical reference numerals designate the same components. Note that the features illustrated in the drawings are not necessarily drawn to scale.

FIGS. 1 and 1a illustrate an embodiment of a MAD with an adjustable mechanism;

FIGS. 2, 2a, 2b and 2c illustrate embodiments of rail and groove portions of an adjustable mechanism;

FIG. 3 illustrates an exploded view of a groove portion with an end stop, a set of spacers and a rail portion of an adjustable mechanism;

FIGS. 4, 4a, 4b, 4c, 4d, 4e, 4f and 4g illustrate embodiments of retaining features for spacers;

FIGS. 5, 5a, 5b and 5c illustrate a mounting device and its use in attaching an adjustable mechanism to a MAD; and FIGS. 6 and 6a illustrate the effect of a MAD on the position of a person's jaws.

DETAILED DESCRIPTION OF THE INVENTION

The detailed description set forth below is intended as a description of the presently exemplified methods, devices, and compositions provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

This invention relates to devices and methods for treatment of sleep apnea and snoring, particularly to devices and methods for mandibular adjustment, and more particularly to devices and methods for adjustable and/or customizable mechanisms for positioning and retaining the upper and lower splints of a mandibular adjustment device (MAD).

Figures 1, 1A, 2, 2A:
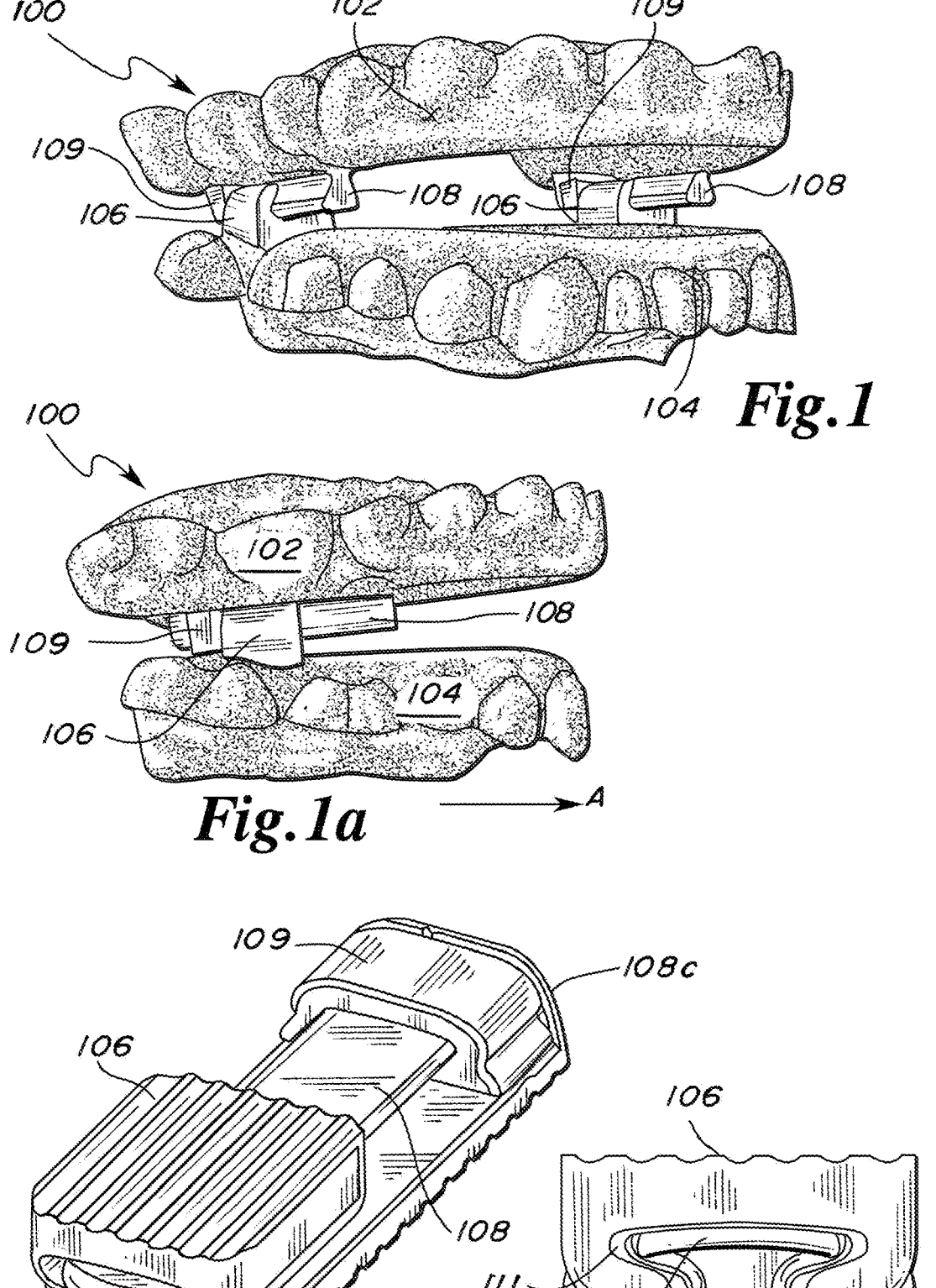

In general, a MAD device may include an upper splint and a lower splint, each for retaining at least a portion of a person's upper jaw (maxilla) and lower jaw (mandible), respectively. FIGS. 1 and 1a illustrate an embodiment of a MAD 100 with an upper splint 102 for accommodating the upper jaw and a lower splint 104 for accommodating the lower jaw. As illustrated, the upper and lower splints 102, 104 may include a channel for retaining the teeth and may be formed to substantially conform to the teeth and/or other anatomical features of a person such that they fit snuggly when the MAD is worn. For example, splints 102, 104 may be formed using molds taken of a patient's upper and lower teeth to make them conformal to the shape of the patient's teeth, such as, for example, using dental impressions. The amount of material and the size of each splint 102 and 104 may depend on the amount of dentition support required to effectively adjust the mandible position of the patient, and in general it may be desirable to utilize enough material to prevent placing undue stress on the person's teeth or mouth. The splints 102, 104 may generally be formed to fit and contour to the jaws of a particular person, however, standardized or generic splints may also be utilized and the splints 102, 104 may generally have an arcuate shape to accommodate the normal shape of human jaws and teeth.

The splints 102, 104 may generally be formed from any appropriate material, such as, for example, acrylic, polycarbonate (PC), polyurethane, polyethylene (PE), polypropylene (PP), polylactic acid (PLA), silicone, nylon, polyvinylchloride (PVC), polyethylene terephthalate (PET), polytetrafluoroethylene (PTFE), acrylonitrile butadiene styrene (ABS), polyether sulphone (PES), polyetheretherketone (PEEK), fluorinated ethylene propylene (FEP), other biocompatible polymers, or any combination thereof.

The splints 102, 104 may generally be manufactured by an appropriate methods, such as, for example, 3D printing, milling, injection molding, and/or other appropriate methods.

The upper and lower splints 102, 104 may generally be operatively coupled together in an arrangement that promotes the positioning of the lower splint 104, and thus the lower jaw of the person, in a more forward position relative to that of the upper splint 102 and jaw in a generally horizontal direction A, as illustrated in FIG. 1a.

In one aspect of the invention, the MAD 100 may include an adjustable mechanism that may vary the relative positioning of the upper and lower splints 102, 104. The adjustable mechanism may generally set the relative horizontal differential between the upper and lower splints 102, 104 such that the lower splint 104 may be set to a desired forward horizontal position relative to the upper splint 102 to treat apnea and/or snoring through protrusive positioning of the lower jaw. In some exemplary embodiments, as illustrated in FIGS. 1 and 1a, the adjustable mechanism may include a rail portion 108 attached to one splint (e.g. upper splint 102 as illustrated) and a corresponding groove portion 106 attached to the other splint (e.g. lower splint 104 as illustrated), with the rail portion 108 and the groove portion 106 mating or interfacing such that the rail portion 108 may slide along the groove portion 106 (or vice versa) to alter the relative positioning of the upper and lower splints 102, 104.

FIGS. 6 and 6a illustrate the effect of the MAD 100 on the positioning of the upper jaw 90 and the lower jaw 92. In FIG. 6 illustrates an example of the jaw positions without the MAD 100 and FIG. 6a illustrates the effect of moving the lower jaw 92 forward of the upper jaw 90 in the horizontal direction A.

Figures 2B, 2C, 3, 4:
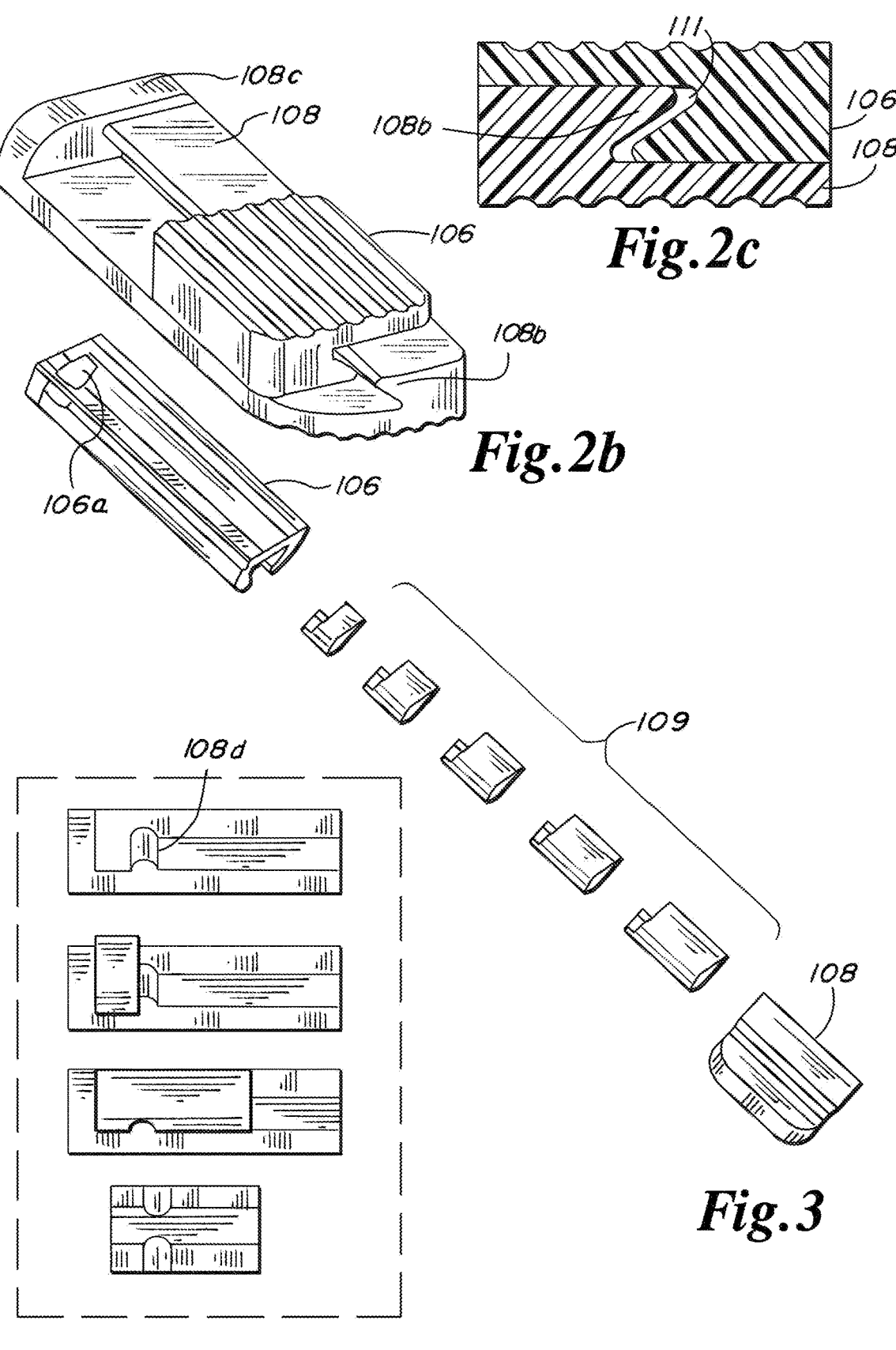

The groove and rail portions 106, 108 may also be shaped in a manner such that the rail portion 108 is retained in the groove portion 106 to prevent the upper and lower splints 102, 104 from separating during use, such as, for example, using corresponding shapes (e.g. male-female connections). FIGS. 2, 2a, 2b and 2c illustrate embodiments of corresponding connections between a rail portion 108 and a groove portion 106. FIGS. 2 and 2a illustrate a dovetail shaped connection with the enlarged section 108a of the rail portion 108 fitting into the corresponding groove portion 106 such that the enlarged section 108a is retained. FIGS. 2b and 2c illustrate another embodiment using a single-sided dovetail shaped connection with enlarged section 108b fitting into corresponding groove portion 106. The groove and rail portions 106, 108 may generally be sized appropriate relative to each other for proper function, for example, with the rail portion 108 being longer and the groove portion 106 being confined to movement along the length of the rail portion 108, or vice versa.

In some embodiments, at least two sets of rail and groove portions 108, 106 may be included to connect the upper and lower splints 102, 104, as shown in FIGS. 1 and 1a. For example, one set may be present on each of the left and right sides of the jaws. The rail and groove portions 108, 106 may generally be attached to upper and lower splints 102, 104 at positions that enable the proper alignment and interfacing of the rail and groove portions 108, 106, such as at the left and right sides of the arcuate form of the splints 102, 104.

In other embodiments, there may be only one set of rail and groove portions 108, 106 connecting the upper and lower splints 102, 104.

The rail portion 108 or groove portion 106 may also generally include a stop to prevent the relative positioning of the upper and lower splints 102, 104 from progressing past a given point. In some embodiments, as illustrated in FIGS. 1, 1a, 2, 2b, the rail portion 108 may include a stop, such as a portion that does not fit into the groove portion 106, as illustrated with rail stop 108c. The stop position may further be adjusted, for example, by placing spacers on the rail portion 108 that may generally extend the stop portion that does not fit into the groove portion 106, as illustrated with the spacer 109 in FIGS. 1, 1a and 2. Spacers 109 may, for example, be of predetermined or metered size, and may be inserted as necessary to vary the stopped position of the lower splint 104 relative to the upper splint 102.

In other embodiments, the groove portion 106 may include a stop, such as with a terminating end of the groove. FIG. 3 illustrates an exploded view of a groove portion 106 having an end stop 106a with a variety of differently sized spacers 109 which may be inserted prior to inserting the rail portion 108. In general, the groove portion 106 may be longer than the corresponding rail portion 108 when spacers 109 are utilized to insert into the groove portion 106.

The spacers 109 and/or the rail portion may also include features to aid in locking the spacers 109 in place such that they are retained on the rail portion 108 or in the groove portion 106, as applicable. For example, features such as friction fitting, retaining ridges 108d as shown in FIG. 4, bumps 108e as shown in FIG. 4a, side hooks 108f as shown in FIG. 4b, under hooks 108g as shown in FIG. 4c, and/or any other appropriate retaining features may be utilized.

In another embodiment, spacers 109 may include a feature that snaps into or is otherwise retained by at least one of a series of depressions. FIGS. 4d, 4e, 4f and 4g illustrate placement of a spacer 109 that includes a snap-in feature 109a retained in a depression 108h on the rail portion 108, with different positions shown by placement into different depressions 108h as shown in FIGS. 4e, 4f and 4g.

In another aspect of the invention, the MAD 100 may include features for enabling small amounts of movement between the upper and lower splints 102, 104. It may be desirable for the connection between the upper and lower splints to be not completely rigid such that the person wearing the MAD may have some degree of jaw mobility, such as to accommodate patients who grind their teeth (bruxism), which involves lateral left/right movement of the lower teeth (mandible) relative to the upper teeth (maxilla), or to aid in, for example and without being bound to any particular theory, preventing stress the Temporomandibular Joint (TMJ), which may cause long term soreness. In some exemplary embodiments, the corresponding shapes of the rail and groove portions 108, 106 of the adjustable mechanism may include some space between them, such as, for example, by the shape of the rail portion 108 being smaller than the corresponding shape of the groove portion 106, such that one portion may move laterally and/or vertically to some degree while interfaced. FIGS. 2a and 2c illustrate examples of the rail portion 108 and groove portion 106 shaped to provide a space 111 such that the rail portion 108 may move within the groove portion 106 to a degree while still being retained.

In a further aspect of the invention, the adjustable mechanism, such as the rail and groove portions 108, 106, may be mounted to the MAD 100 utilizing a device that enables adjustment of the positioning and/or orientation of the adjustable mechanism relative to the upper and lower splints 102, 104 such that the proper horizontal movement is enabled. This may be desirable as the upper and lower splints 102, 104 may not have corresponding parallel surfaces when in place in a person's mouth.

In some exemplary embodiments, as illustrated in FIG. 5, a mounting device 200 may include an aperture 202 for the groove portion 106 of the MAD 100 to pass through to retain the groove portion 106, and an aperture 204 for insertion of the rail portion 108 such that the rail portion 108 may also interface with the groove portion 106. This may be utilized during the attachment of the adjustable mechanism to the upper and/or lower splint(s) 102, 104 to ensure their proper alignment and positioning when they are attached, such as, for example, to accommodate non-parallel interfacing of the upper and lower splints 102, 104.

The mounting device 200 may also include an adjustable section 206 such that the mounting device 200 may be adjusted in size laterally, as illustrated in direction B in FIG. 5a, to accommodate different widths of the splints 102, 104, which may vary due to differing jaw shapes and sizes from different people. In some exemplary embodiments, the mounting device 200 may be constructed from two identical components, each of which may include a male and female portion to enable interfacing with another identical component in a different orientation. This may be utilized, for example, to form the adjustable section. FIG. 5b illustrates a single component 210 with a male connection 212 and a female connection 214 such that it may connect with another component 210 to form the mounting device 200 with lateral adjustability along the interface between the male and female connections 212, 214.

Figure 5C:
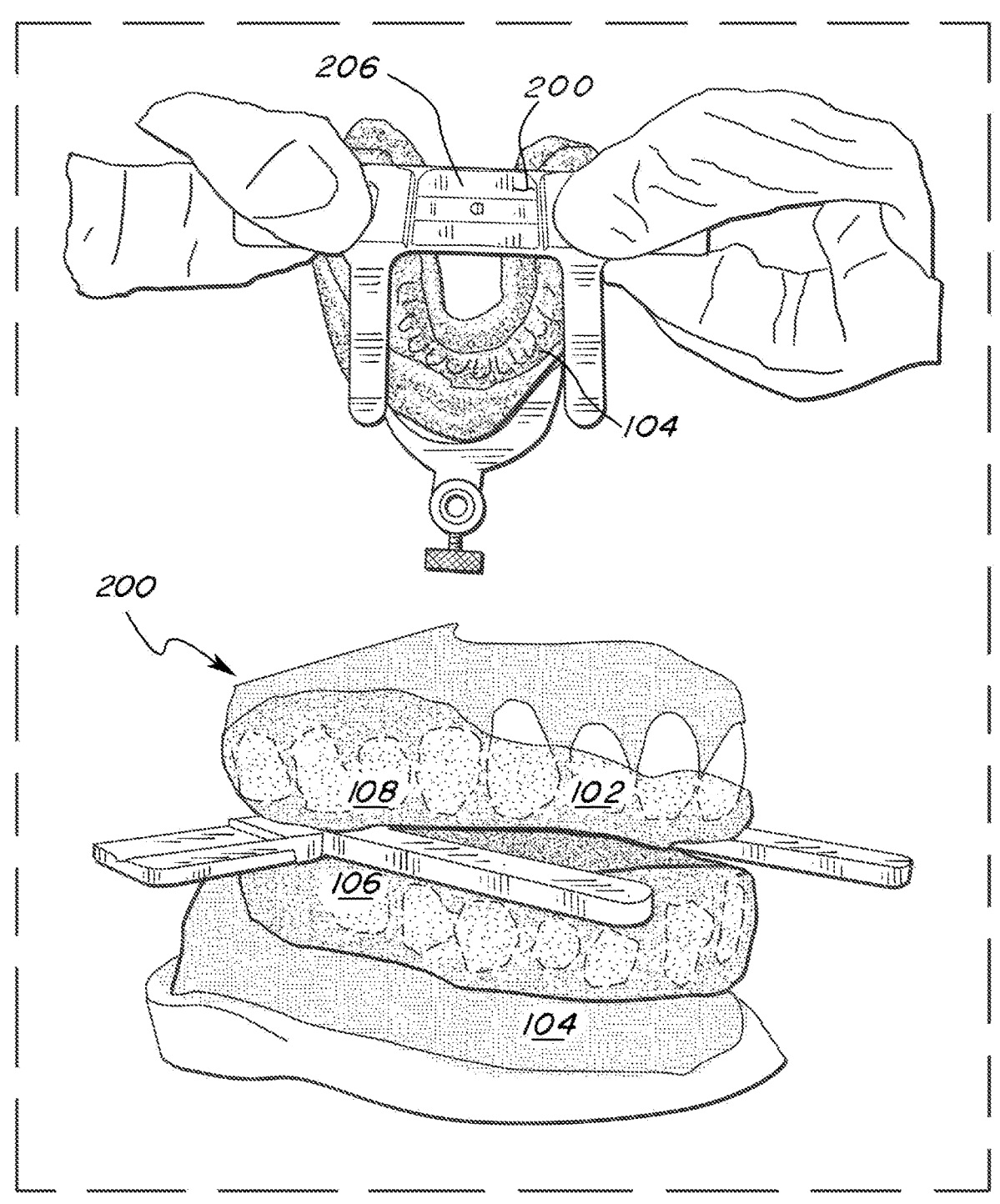

In some embodiments, one of the splints, such as the lower splint 104, may be placed in a retaining frame or device, as illustrated in FIG. 5c, and the rail and groove portions 108, 106 inserted into the mounting device 200 may be placed and adhered to the lower splint 104. The upper splint 102 may further be positioned in the proper position relative to the lower splint 104 and adhered to the upper portion of the rail and groove portions 108, 106. The mounting device 200 may then be removed once the adhesion is complete by sliding out the rail portion 108, thus releasing the groove portion 106 and the mounting device 200. An appropriate adhesion method, such as adhesives, heat welding, cross-linking or polymerization, and/or any other appropriate adhesion method may be utilized.

In some embodiments, the rail and groove portions 108, 106 may also be formed integrally or co-manufactured with the splints 102, 104, such as by 3D printing, milling, injection molding, and/or other appropriate methods.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

The invention claimed is:

1. A device for adjusting mandibular position comprising:
an upper splint configured to receive at least some of a patient's upper teeth;
a lower splint configured to receive at least some of the patient's lower teeth;
an upper interface attached to said upper splint, said upper interface comprising at least one rail; and
a lower interface attached to said lower splint, said lower interface comprising at least one groove, wherein one of said at least one grooves is adapted to interface with one of said at least one rails by insertion of a front end of said rail into said groove to form at least one rail and groove connection that is adapted such that said rail may slide along said groove in a horizontal direction to alter positioning of said upper and lower splints relative to each other in said horizontal direction to project said lower splint forward in said horizontal direction relative to said upper splint, said rail being longer than said groove and comprising a stop formed on a rear end of said rail that is enlarged to prevent further sliding of said rail in said groove past said stop;

wherein said rail and said groove are shaped to prevent substantial vertical separation of said upper and lower splints after insertion of said rail into said groove.

2. The device of claim 1, wherein said at least one rail and groove connections further comprises two of said rails and two of said grooves.

3. The device of claim 2, wherein said at least one rail and groove connection comprises a left and right set.

4. The device of claim 3, wherein said left and right sets are connected to said upper and lower splints at left and right sides of an arcuate portion of said upper and lower splints.

5. The device of claim 1, further comprising at least one spacer adapted to adjust said positioning by extending said stop on said rail.

6. The device of claim 5, wherein said at least one spacer comprises a feature for locking in said spacer on said rail.

7. The device of claim 6, wherein said feature for locking in said spacer comprises a snap-in interface.

8. The device of claim 1, wherein said at least one rail and groove connections comprises lateral space between said rail and groove from at least a portion of said rail being smaller than a corresponding portion of said groove and formed to allow said rail and groove to move laterally and vertically relative to each other when interfaced.

9. The device of claim 1, wherein said upper and lower splints are configured to rest in a non-parallel orientation relative to each other when said upper and lower interfaces interconnect.

10. The device of claim 1, wherein said rail comprises a dovetail-shaped rail and said groove comprises a corresponding-shaped groove.

11. The device of claim 1, wherein said device is constructed from a material selected from the group consisting of acrylic, polycarbonate (PC), polyurethane, polyethylene (PE), polypropylene (PP), polylactic acid (PLA), silicone, nylon, polyvinylchloride (PVC), polyethylene terephthalate (PET), polytetrafluoroethylene (PTFE), acrylonitrile butadiene styrene (ABS), polyether sulphone (PES), polyetheretherketone (PEEK), fluorinated ethylene propylene (FEP), and combinations thereof.

12. The device of claim 1, wherein said rail is attached to said upper splint and said groove is attached to said lower splint by adhesive.

13. The device of claim 1, wherein said groove is open on a front end and a back end.

14. The device of claim 1, wherein said rail comprises a single-sided dovetail-shaped rail and said groove comprises a corresponding-shaped groove.

15. A method for customizing a device for adjusting mandibular position comprising:
providing an upper and lower splint configured to receive at least some of a patient's upper and lower teeth, respectively;
attaching a first and a second rail to said upper splint and attaching a first and a second groove to said lower splint such that said lower splint is configured to be biased forward in said patient's mouth relative to said upper splint when said first and second rails are inserted into said first and second grooves to form a first and a second rail and groove connection, respectively, said rails being longer than said grooves and adapted such that said first and second rails may slide along said first and second grooves, respectively, to alter horizontal positioning of said upper and lower splints relative to each other that are shaped to retain each other in connection and said rails each comprising a stop formed on a rear end of each of said rails that is enlarged to prevent further sliding of said rails in the respective said grooves past said stop; and utilizing a mounting device to retain and adjust the position of said rail and groove connections relative to said upper and lower splints to adjust the fit and positioning of said upper and lower splints relative to each other for use by said patient, said mounting device comprising two substantially identical portions that interconnect with each other via corresponding male and female connection portions and each having apertures shaped for retaining one of said rail and groove connections, wherein said mounting device is wholly separate and removable from said upper and lower splints and said rail and groove connections after said positioning.

16. The method of claim 15, further comprising adjusting said fit and positioning of said upper and lower splints relative to each other for use by said patient by addition of at least one spacer.

17. The method of claim 15, wherein said mounting device adjusts laterally to accommodate differing widths of jaws and arcuate portions of said upper and lower splints.

18. The method of claim 15, further comprising adhering said rails and grooves to said upper and lower splints and removing said mounting device after said adhering.

19. The device of claim 15, wherein said rails and grooves are adhered to said upper and lower splints in a configuration to enable sliding of said rails and grooves relative to each other in an approximately horizontal direction.

20. The method of claim 15, wherein rails and grooves are adhered in a configuration such that said upper and lower splints rest in a non-parallel orientation relative to each when said rails and grooves interconnect.

* * * * *